United States Patent [19]

Paracchini et al.

[11] 4,379,935
[45] Apr. 12, 1983

[54] PROCESS FOR THE SYNTHESIS OF VINCAMINE AND RELATED INDOLE ALKALOIDS

[75] Inventors: Silvano Paracchini, Codogno Milano, Italy; Paolo C. Mora, Via Scalabrini 49, Piacenza, Italy

[73] Assignee: Paolo Corvi Mora, Piacenza, Italy

[21] Appl. No.: 288,419

[22] Filed: Jul. 30, 1981

[30] Foreign Application Priority Data

Aug. 4, 1980 [IT] Italy ................ 23904 A/80

[51] Int. Cl.³ .................. C07D 461/00; C07D 455/00
[52] U.S. Cl. .......................................... 546/51; 546/70
[58] Field of Search ................ 546/51, 70; 424/256

[56] References Cited

U.S. PATENT DOCUMENTS 3,755,333  8/1973  Szantay et al. ............... 546/51
4,033,969  7/1977  Sevenét et al. ............... 546/51
4,267,330  5/1981  Kuehne ........................ 546/51

Primary Examiner—Donald G. Daus
Assistant Examiner—Diana G. Rivers
Attorney, Agent, or Firm—Murray and Whisenhunt

[57] ABSTRACT

A process is taught for the synthesis of vincamine and related indole alkaloids, according to which, through only two steps and through a novel synthesis intermediate, namely the glycidic ester, having the formula

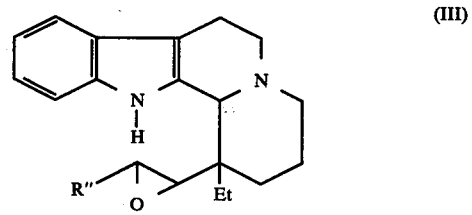

(III)

wherein R" represents —COOCH₃ or —COOCH₂CH₃, 1-ethyl-1,2,3,4,5,6,7,12b-octahydroindole[2,3-a]quinolizine-1-carboxaldehyde is reacted with a haloester in the presence of a base and the glycidic ester is converted to vincamine or apovincamine or like esters by reaction with a Lewis acid or a mineral acid, the reaction products being subsequently separated by chromatography.

6 Claims, No Drawings

PROCESS FOR THE SYNTHESIS OF VINCAMINE AND RELATED INDOLE ALKALOIDS

The present invention relates to a process for the preparation of the optical isomers and of the racemic forms of the vincamine and of the related indole alkaloids, as represented by the formula:

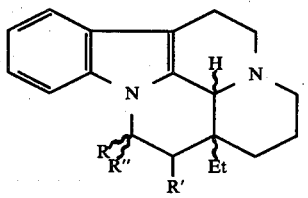
(I)

wherein:
when R=OH, R'=H, and R''=—COO CH$_3$, the compound (I) is vincamine and its optical isomers;
when R=OH, R'=H and R''=—COOCH$_2$CH$_3$, the compound (I) is ethyl vincaminate and its optical isomers;
when R+R'=double bond, and R''=—COOCH$_3$, the compound (I) is apovincamine and its optical isomers;
when R''=R'=H and R=OH, the compound (I) is vincanol and its optical isomers.

It is known that the vincamine and the indole alkaloids related thereto, which are covered by the present invention, are endowed with interesting therapeutical properties, at the cardiovascular level and generally for the circulatory system. More particularly the vincamine and the apovincamine are substances already known and used in the therapy of the cerebral arteriosclerosis, owing to their efficacious vasodilating action at the cerebral level and also owing to their capability in activating the metabolism of the nervous cells.

The starting compound for the preparation of the compounds (I) is represented by the forumla (II)

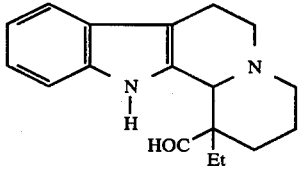
(II)

The method for the preparation of the sintone (II), both as the racemic mixture of the diastereoisomers, and in form of the single, optically pure isomers, has been described by W. Oppolzer et al., Helv. Chim. Acta, 60(5), 1801(1977). For the conversion of the aldehyde (II) to vincamine, the prior art (W. Oppolzer) discloses the following process:

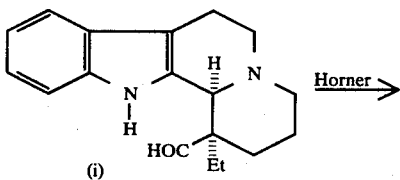

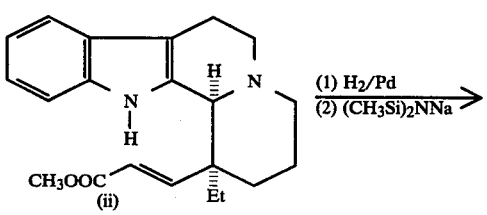

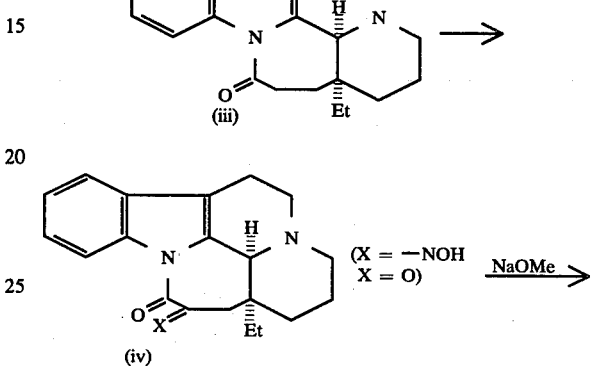

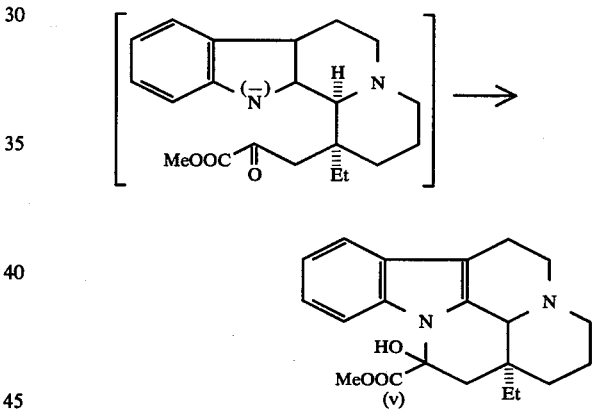

According to the preceeding scheme, the aldehyde (i) is converted to the corresponding ethylester acrylate, by treatment with triethylphosphonium acetate under the reaction conditions taught by Horner.

The ester (ii) is firstly catalytically reduced and then condensed to give the homoeburnamonine (iii), which with butylnitrite in the presence of bis-trimethylsilylamide in toluene gives the oxime (iv) (X=—NOH).

The oxime is then hydrolized with HCL in the presence of formaldehyde, the homoeburnamonin-15-one (iv) (X=O) being isolated from the reaction mixture.

By alkaline splitting of the diketone iv) (X=O) and acification of the resulting, reaction mixture, the vincamine (v) is isolated.

It has been now found a novel process which permits the compounds represented by the formula (I) to be prepared starting from the compound (II) through only two steps according to the following scheme:

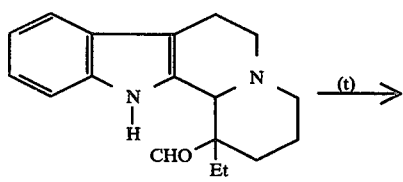

(II)

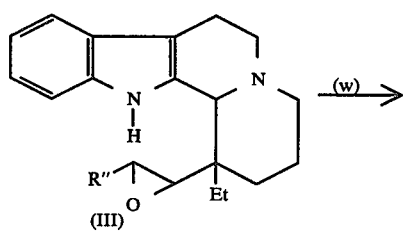

(III)

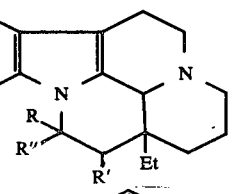

(I)

wherein R, R' and R" have the above indicated meanings.

In the step (t) the aldehyde (II) is converted to the glycidic ester (III), this compound having never been described in the prior art, by treatment with a haloester of the type

wherein X=Cl, Br, I; R"=—COOCH$_3$, or —COOCH$_2$CH$_3$, in the presence of a base, such as sodium or potassium alcoholates, by using as the solvent anhydrous ethers or hydrocarbons, and carrying out the reaction at temperatures of between 0° C. and 10° C. Subsequently, if the compound (III) is reacted (step w) with a Lewis acid such as BF$_3$ in toluene at 50°–100° C., it is possible to isolate by means of column chromatography from the reaction mixture, provided that the latter is processed in conventional way, the compounds (I), the groups R, R' and R" having the above stated meanings, except for the case of R=R'=H and R"=OH, whereas if the compound (III) is reacted with a diluted mineral acid at 50°–80° C., by column chromatography of the reaction raw mixture it is possible to isolate, besides the other compounds, also the product (I) in which R=R'=H and R"=OH.

The process of the invention can be thus represented in the following form:

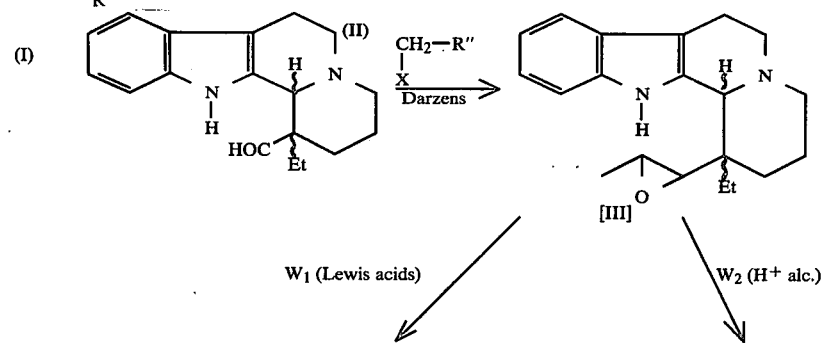

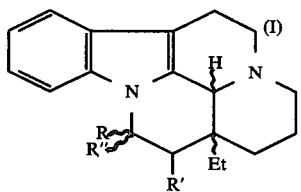

I: R = OH; R' = H; R" = COOY
R + R' + double bond R" = COOY
Y = methyl or ethyl

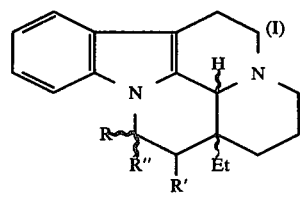

I: R—OH, R' = H; R" = COOY
R + R' = double bond, R" = COOY
Y = methyl or ethyl;
R = OH, R = R" = H The process for the preparation of the compounds (I), which is the subject of the present invention, is thus based on the intermediate (III), which as such is also a subject of the present invention, since it has never been previously described, both as a compound and as an intermediate for the production of the compounds (I).

EXAMPLE 1

Preparation of ethyl vincaminate (I: R=OH; R'=H, R''=COOC₂H₅), of ethyl apovincaminate (I:R+R'=double bond, R''=COOC₂H₅) and of vincanol (I:R=R'=H, R''=OH).

1.1- Preparation of the glycidic ester (III)

ethyl-1-ethyl-1,2,3,4,5,6,12b-octahydro-indole-[2,3-a]-quinolizine 1-(1'2' oxy)-propionate

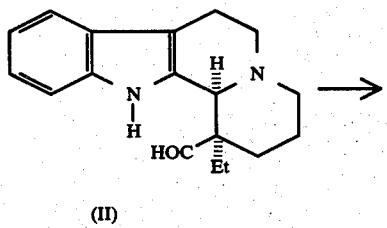

(II)

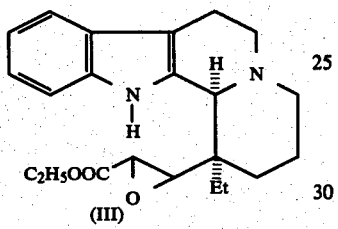

(III)

In a suitable tank a solution is prepared comprising 2 g of aldehyde (II), 1.3 g of ethyl chloroacetate and 100 mls of anhydrous ethyl ether.

0.52 g of sodium amide are subsequently added in small portions over 30 to 60 minutes, the mixture being maintained under an atmosphere of inert gas and at 0° C.

At the end of the reaction, the mixture is brought to room temperature and poured in iced water.

The product is extracted with CH₂Cl₂, and the resulting organic phase is washed with water saturated with salt, dried over Na₂SO₄, filtered and concentrated to a dry residue. There are obtained about 1.1 g of raw product which, without need of being isolated, is directly passed to the subsequent treatments.

(1.2-a) Treatment with Lewis acid 1.1 g of the residue resulting from the reaction 1.1 are dissolved in anhydrous toluene (30 mls).

The resulting solution is added with 10 mls of boron trifluoride etherate and the mixture is heated to 80° C. under stirring. At the end of the reaction, the solution is cooled, filtered and concentrated under vacuum.

The residue is treated by column chromatography, by using as the eluant a mixture of acetone/methylene chloride/methanol in the ratios 5/4.9/0.1 and silica gel as the adsorbant.

From the eluate of the column, after concentration to dryness of the useful fractions and subsequent crystallization, the following products are serially recovered:

(1) ethyl apovincaminate (I:R+R'=double bond, R''=COOC₂H₅).

(2) ethyl vincaminate (I:R=OH, R'=H, R''—COOC₂H₅)

(1.2-b) Treatment with mineral acids

The conversion is carried out as in the example 1.2-a), by using 20 mls of 10% HCl in alcohol, instead of the BF₃ etherate.

At the end of the reaction, the mixture is made alkaline by adding sodium methoxide, filtered and concentrated under reduced pressure to a residue.

The residue is treated by column chromatography, under the conditions of the preceding example (1.2-a).

From the eluate of the column the following products are serially recovered:

(1) ethyl apovincaminate
(2) ethyl vincaminate
(3) ethyl epivincaminate
(4) vincanol (I:R=OH, R'=R''=OH).

We claim:

1. A process for the preparation of vincamine and related indole alkoloids of the formula (I)

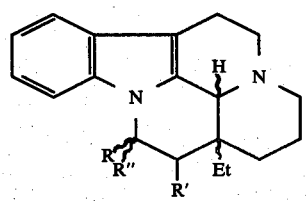

wherein:

(a) R is —OH, R' is H, and R'' is COOY wherein Y is selected from the group consisting of —CH₃ and —CH₂CH₃;
(b) R is —OH, and both R' and R'' are H; or
(c) R'' is COOY, and R and R' together form a double bond, said process comprising reacting a compound of the formula (II)

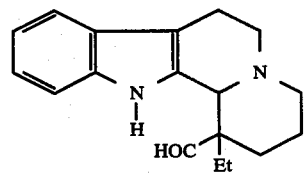

with an alpha-halo-ester of the formula CH₂X-R'' wherein X is selected from the group consisting of Cl, Br, and I and R'' is COOY, in the presence of a base containing at least one member selected from the group comprising alkaline alcoholates and metal amides where the metal is selected from the group consisting of Na, K, or Li, according to the Darzens reaction conditions, to give the corresponding glycidic esters of the formula (III)

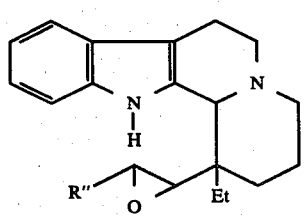

and thereafter treating the glycidic ester with a Lewis acid in an inert solvent and/or with a mineral acid in alcoholic solution to produce a compound of formula (I).

2. A process according to claim 1, characterized in that, for the isolation of the reaction products, the raw reaction mixture is treated by column chromatography.

3. A process according to claim 1, characterized in that the Darzens reaction is carried out in an inert solvent selected from a group consisting of anhydrous ethers and hydrocarbons, at a temperature of between 0° and 10° C.

4. A process according to claim 1, where said Lewis acid is a solution consisting of boron trifluoride etherate and toluene, said solution being used to treat the glycidic ester of formula III to yield the desired compound of formula I, said process being carried out at a temperature between 50° and 100° C.

5. A process according to claim 1, characterized in that the treatment of the glycidic esters (III) to give the desired compounds (I) is carried out with mineral acids in alcoholic solution at a temperature of between 40° and 90° C.

6. Glycidic esters represented by the formula (III):

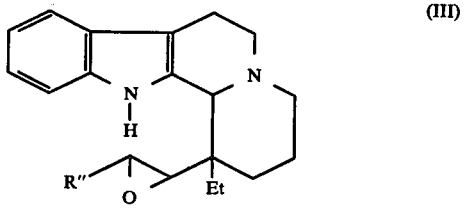

wherein R" is —COOCH$_3$ or —COOCH$_2$CH$_3$.

* * * * *